United States Patent [19]

Siewert et al.

[11] Patent Number: 5,589,690
[45] Date of Patent: Dec. 31, 1996

[54] APPARATUS AND METHOD FOR MONITORING CASTING PROCESS

[75] Inventors: Thomas A. Siewert, Boulder; William P. Dubé, Denver; Dale W. Fitting, Golden, all of Colo.

[73] Assignee: National Institute of Standards and Technology, Washington, D.C.

[21] Appl. No.: 407,699

[22] Filed: Mar. 21, 1995

[51] Int. Cl.⁶ ..................................... G01N 23/20
[52] U.S. Cl. .................. 250/390.06; 250/390.09; 378/71
[58] Field of Search ................. 378/70, 73, 86, 378/71, 6; 250/390.09, 390.06

[56] References Cited

U.S. PATENT DOCUMENTS

| | | | |
|---|---|---|---|
| 3,499,736 | 3/1970 | Zwaneburg | 23/301 |
| 3,790,252 | 2/1974 | Pao | 350/160 R |
| 3,833,810 | 9/1974 | Efanov et al. | 250/273 |
| 4,284,887 | 8/1981 | Kusumoto et al. | 250/272 |
| 4,634,490 | 1/1987 | Tatsumi et al. | 156/601 |
| 4,696,024 | 9/1987 | Pesch | 378/71 |
| 4,710,259 | 12/1987 | Howe et al. | 156/601 |
| 5,016,266 | 5/1991 | Meurtin | 378/73 |
| 5,093,573 | 3/1992 | Mikoshiba et al. | 250/310 |
| 5,136,624 | 8/1992 | Schneider et al. | 378/73 |
| 5,193,104 | 3/1993 | Bastie et al. | 378/73 |

FOREIGN PATENT DOCUMENTS 642638  1/1979  U.S.S.R. ............... 378/73

OTHER PUBLICATIONS

"X-Ray Diffraction", Physical Metallurgy Principles by Reed-Hill, pp. 26–33.
Baxter et al., "Rapid Orientation Measurement of Single Crystal Casting Using 'Scorpio'", Insight, vol. 36, No. 5, May 1994.
Hashizume et al, "Techniques for Time-Resolved X-Ray Diffraction Using a Position Sensitive Counter", Japanese J. Appl. Phys., 15, (11), Nov. 1976, pp. 2211–2219.

*Primary Examiner*—Carolyn E. Fields
*Attorney, Agent, or Firm*—Sheridan Ross & McIntosh

[57] ABSTRACT

The present invention uses a high energy x-ray, neutron, or gamma source for monitoring the interface between a molten and solidified crystalline phase while in a furnace in a casting process. The radiation can also be used to determine the quality and orientation of the crystals in the crystalline phase. The invention uses the distinctive diffraction patterns produced by crystalline and amorphous phases to locate the interface.

25 Claims, 4 Drawing Sheets

APPARATUS AND METHOD FOR MONITORING CASTING PROCESS

FIELD OF THE INVENTION

The present invention relates generally to an apparatus and method for monitoring the casting or thermal treatment of materials, and more particularly, for monitoring the liquid amorphous/solid crystalline interface in a material being cast so as to permit process control parameters to be established and/or controlled in response thereto.

BACKGROUND OF THE INVENTION

Advancements in materials processing technology have caused an increasing demand for parts made from superalloys. Many high performance aircraft, for example, now employ turbine blades that are single crystals of nickel-based superalloys. The desirability of superalloys results from their high strength at high operating temperatures.

Superalloy parts are typically produced as single-crystal or directionally-solidified castings. Elaborate casting and inspection methods are employed to ensure that each part is a single-crystal or directionally-solidified crystal with a desired orientation. Even minor defects in the crystalline structure may be unacceptable as they can result in mechanical failure.

To reduce the likelihood of defects in the crystalline structure, the casting process for such parts has become a labor and time intensive process. The molten alloy is poured into a mold located in a furnace. One end of the mold is cooled to initiate crystallization. The mold is then slowly withdrawn from the furnace. The withdrawal rate is extremely slow to ensure an acceptable crystallization rate and crystal of the correct orientation. A slow crystallization rate promotes flawless crystal growth in the direction of solidification. If the rate of crystallization is too rapid, the metal will form unacceptable polycrystals and the part must be discarded. The possibility of forming parts with defects in the crystal structure with a lack of a reliable technique to otherwise monitor the rate of crystal growth during casting has to date caused engineers to select extremely conservative (i.e., slow) crystallization rates.

Further, despite the noted precautions taken during casting, defects can still occur which result in discarded parts and wasted production time. The scrapped material cannot simply be remelted and reused but must rather be retreated by an expensive refinement process before further use.

SUMMARY OF THE INVENTION

It is an objective of the present invention to provide an apparatus and method for real time monitoring of the interface between the solid crystalline and liquid amorphous phases of a material being cast in a mold during casting, thereby allowing for an increase in throughput and decrease in production costs. It is a related objective to provide a monitoring apparatus and method to permit casting process control parameters to be established and/or controlled in response thereto, wherein the process provides optimal conditions for the desired crystal formation.

It is a further specific objective to increase throughput and decrease the production costs of single-crystal and directionally-solidified castings by decreasing the time required to form such castings and minimizing the occurrence of defects and flaws in the castings. As will be appreciated, the present invention is particularly useful for monitoring the interface between molten (i.e., liquified) and solidified states of materials, such as alloys of iron, titanium, nickel, and aluminum, ceramics, semiconductors, such as silicon, germanium, gallium arsenide, cadmium telluride, cadmium sulfide, and indium phosphide.

By way of initial summary, the present invention includes: (i) directing source radiation through a casting mold and into an interface between a portion of the crystalline phase and amorphous phase of a material being cast to provide diffracted radiation having a first component associated with the crystalline phase and a second component associated with the amorphous phase; (ii) receiving at least a portion of at least one and preferably both of the first component and second component of the diffracted radiation outside of tile casting mold and providing an output signal in response thereto; and (iii) using the output signal to monitor the interface between the crystalline and amorphous phases.

Preferably, x-ray radiation is employed and, as will be further discussed, the energy and intensity of the source radiation should be sufficient to penetrate the mold/cast material and to otherwise provide the diffracted components at an intensity sufficient for associated detection by a radiation-sensitive receiver means such as one or more x-ray imager(s) or energy detector(s). The casting mold can be composed of either amorphous or crystalline materials provided that the container is penetrable by the source radiation and stable at the melting point of the cast material. Suitable container materials include, for example, sand, alumina, zirconia, quartz, graphite, ceramics, and more particularly, aluminum oxide, zirconium oxide, and other metal oxides. Additional intervening structures, such as the walls of a furnace, can be present between the radiation source and diffracted radiation receiver, provided that such structures do not block or otherwise unduly attenuate the source and/or diffracted radiation.

The first and second components of the diffracted radiation result from the differing manners in which the amorphous phase and crystalline phase of the cast material diffract the source radiation. Briefly, the crystalline phase produces a radiation diffraction pattern comprising concentrated radiation areas, or high-intensity spots, while the amorphous phase produces a more diffuse and lower intensity ring pattern. Consequently, the radiation-sensitive receiver means should be positioned so as to receive at least a portion of one and preferably both of said concentrated radiation and diffuse radiation associated with the crystalline and amorphous phases, respectively.

In this manner, e.g., the output signal of the radiation-sensitive receiver means will reflect, on a real-time basis, an increase over time in the received diffracted radiation associated with an increasing crystalline phase. More preferably, e.g., by receiving a portion of both the diffracted radiation associated with an increasing crystalline phase and the diffracted radiation associated with the decreasing amorphous phase, the output signal can reflect the increase of the diffracted radiation received from the crystalline phase relative to that received from the amorphous phase. In this regard, the output signal may include a first output signal component corresponding with the first diffracted radiation component that is received and a second output signal component corresponding with the second diffracted radiation component that is received.

As will be appreciated then, use of the output signal to monitor the crystalline phase/amorphous phase interface generally entails (i) generating for successive time intervals corresponding successive values corresponding with at least one or preferably both of a first output signal component corresponding to the first diffracted radiation component and a second output signal component corresponding to the second diffracted radiation component; and (ii) employing the successive values to monitor the state and/or progression of the phase interface. More particularly, the successive values can be compared to predetermined completion values that correspond with associated degrees of crystallization completion, as determined by prior design testing.

For example, to determine the position of the interface as a function of time, the process can include the steps: (i) comparing during a first time interval the first and second output signal components to locate the interface at a first position; (ii) comparing during a second time interval the first and second output signal components to locate the interface at a second position; and (iii) employing the first and second positions to monitor the phase interface. The position of the interface can be estimated based upon the magnitude of the first and/or second output signal components. For example, the magnitude of the first output signal component can be compared to a predetermined magnitude corresponding with the diffraction pattern of a complete crystalline phase in the mold and/or the magnitude of the second output component can be compared to a predetermined magnitude corresponding with the diffraction pattern of a complete amorphous phase in the mold to locate the point below which the material in the container is substantially crystalline or above which the material in the container is substantially amorphous.

Further, the above-noted successive values can be successively compared to either predetermined completion values or to each other to determine a rate of crystallization. Such determination may include, e.g., (i) comparing during a first time interval a first output signal component (corresponding with the received portion of the first component of the diffracted radiation) with a second output signal component (corresponding to the received portion of the second signal component of the diffracted radiation) to provide a first compared value; (ii) comparing during a second time interval the first output signal component with the second output signal component to provide a second compared value; and (iii) employing the first and second compared values to determine a rate of crystallization. The rate of crystallization can be compared to predetermined rate values to monitor when crystallization is complete (e.g., as rate approaches zero) and/or to otherwise monitor if crystallization is occurring at a desired rate (e.g., to ensure the desired crystal structure).

As will be appreciated, by monitoring the crystalline phase/amorphous phase interface, a monitor signal can be generated for real-time control of at least one of the following casting process parameters: the temperature of a furnace containing the mold and the rate of withdrawal of the cast material from the furnace.

The present invention can be used not only to provide real-time monitoring and control of a casting process but also to verify in the laboratory casting process models leading to the establishment of casting process control parameters to yield substantially optimal conditions for crystal formation. The performance of casting under substantially optimal conditions reduces both the frequency of defects and/or flaws in the crystal structure of the part and the labor and time requirements to produce the part. These reductions substantially reduce the production costs of the parts relative to existing casting processes.

DETAILED DESCRIPTION

The present invention provides an apparatus and method for the real-time monitoring of the interface between a crystalline phase, such as a solidified metal, and an amorphous phase, such as a molten metal, while contained in a mold. The interface is monitored by comparing the distinctly different radiation diffraction patterns produced by a crystalline phase compared to an amorphous phase. As discussed in detail below, the highly ordered crystal structure of the crystalline phase will produce a radiation diffraction pattern that includes a number of distinct spots and energy peaks while the relatively disordered structure of an amorphous phase will produce a radiation diffraction pattern that is a diffuse ring pattern with no distinct spots or energy peaks. Thus, the two phases produce radiation diffraction patterns that are distinct in geometry, intensity, and energy distribution. Although materials in the mold can produce interfering spots or rings, the radiation diffraction pattern produced by the mold is known, or is measurable, and can therefore be removed from or otherwise accounted for in the measured diffraction pattern.

Figure 1:
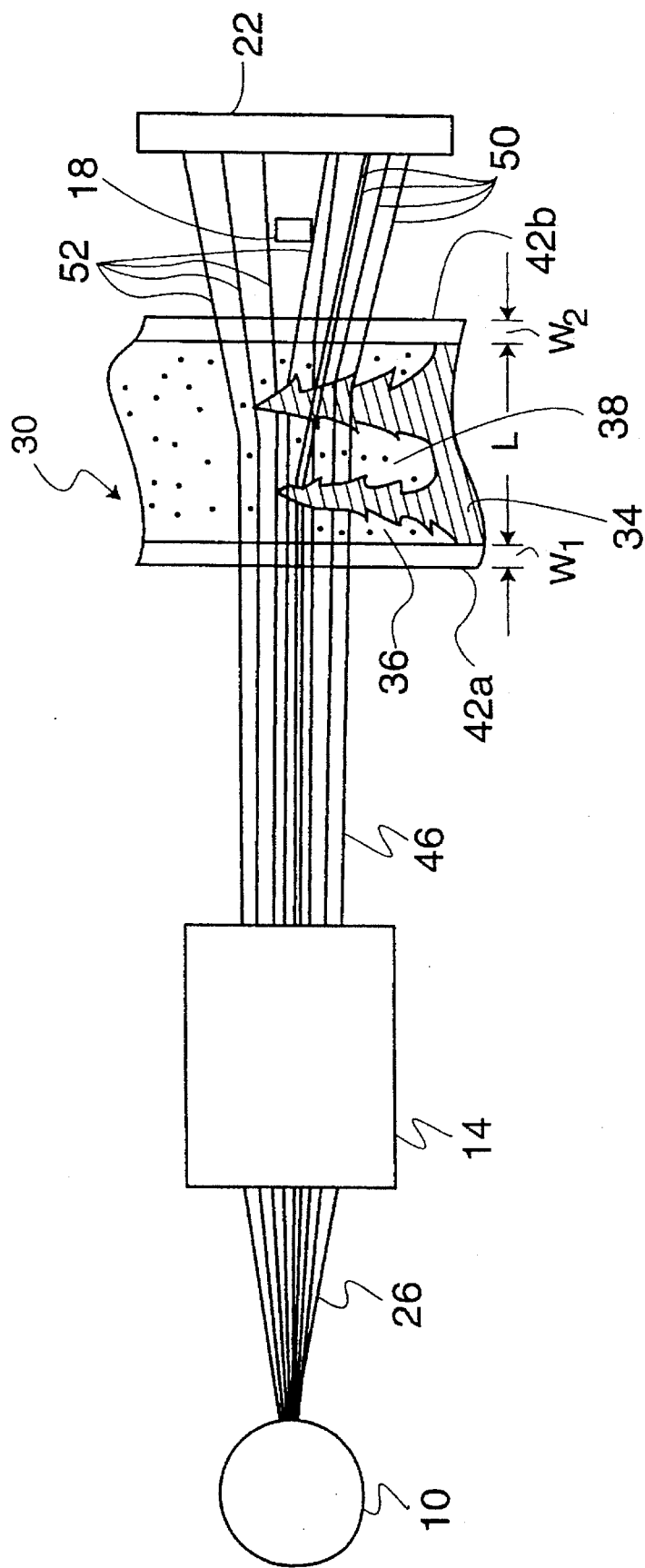
FIG. 1 illustrates one embodiment according of the present invention.

FIG. 1 depicts an embodiment according to the present invention. The embodiment includes an x-ray radiation source 10, a collimator 14, a beam stop 18, and a detector assembly 22. The radiation source 10 produces x-ray source radiation 26 of a relatively high energy and intensity to penetrate a sample section 30, which includes the crystalline and amorphous phases 34, 38, and mold walls 42a,b. The collimator 14 restricts the source radiation 26 to a narrow range of angular orientations. This collimated radiation 46 has a plurality of substantially parallel x-rays. The beam stop 18 absorbs undiffracted and other radiation that has passed through the mold walls 42a,b and sample section 30 within a predetermined angular or spatial range. The detector assembly 22 receives a first component 50 of the diffracted radiation associated with the crystalline phase and a second component 52 associated with the amorphous phase and provides an output signal related to the first and second components.

The radiation source 10 can be any suitable x-ray, neutron, or gamma source for producing radiation having energy levels sufficient to penetrate the mold walls 42a,b, sample section 30, and any other intervening structure and a sufficient intensity to provide a diffraction pattern from the sample section 30 at the detector assembly 22 that is distinguishable from other incident radiation, such as non-diffracted radiation not absorbed by beam stop 18, leakage from the radiation source 10, and radiation diffracted by intervening structures, such as the mold walls 42a, 42b. More particularly, the energy level of radiation source 10 should be selected so that the collimated radiation 46 will travel through the first mold wall 42a, and a portion of the sample section 30 so as to permit at least a portion of the radiation to undergo a coherent interaction with the crystalline phase 34 and/or amorphous phase. Further, the first and second components of the diffracted radiation (e.g., coherent radiation) must then penetrate the remainder of the sample section and the second mold wall 42b.

In selecting the energy of the radiation source 10, there is a tradeoff between achieving adequate transmission of the radiation through the mold walls 42a,b and other intervening surfaces and the sample section 30 (the degree of transmission of radiation is greater at higher energies and lower at lower energies) and obtaining a sufficiently large cross-section for the first and second components of the diffracted radiation (the probability of coherent interactions and therefore the quality of the diffraction image produced by the detector assembly is higher at lower energies than higher energies). At excessively high energies, Compton scattering of the radiation, which is substantially forward directed, can be a problem.

In selecting the intensity of the radiation source, the diffracted radiation received by the detector assembly 22 must have sufficient intensity to be separated from background noise. Background noise is typically caused by radiation diffracted by intervening structures, such as the mold, leakage radiation from the radiation source, Compton scatter from the sample and structures surrounding the sample (e.g., mold, furnace), and non-diffracted radiation that is not fully absorbed by the beam stop 18. It is necessary to select the radiation source intensity such that the intensity of the diffracted pattern exceeds the intensity of the background noise.

In view of the foregoing, in selecting both the energy and intensity of the radiation source 10, the thicknesses and compositions of the sample section 30 and mold walls 42a,b and other intervening structures (e.g., furnace walls) can be measured and otherwise accounted for. These properties are important for predicting losses in the structures.

Figure 2:
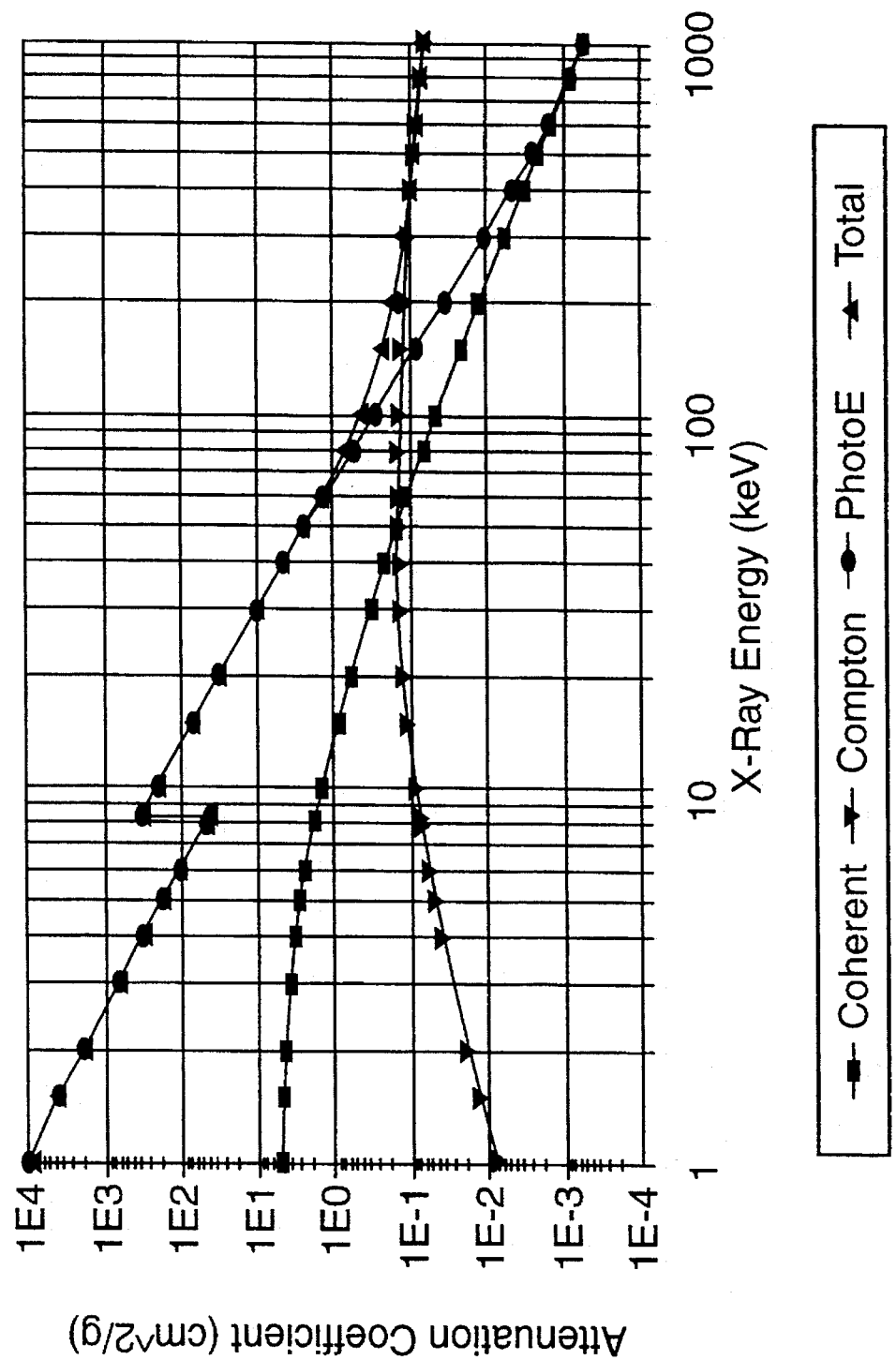
FIG. 2 is a plot of the mass attenuation coefficients of nickel versus the energy of the source radiation.

Relatedly, the total mass attenuation coefficients for the sample section 30, mold 42, and other intervening structures can be determined for a predetermined range of source radiation energies utilizing known values. By way of example, FIG. 2 sets forth partial and total mass attenuation coefficients for nickel. As can be seen from FIG. 2, the mass attenuation coefficients are a function of the source radiation energy.

After determining the total mass attenuation coefficients for the sample section 30, mold 42, and other intervening structures and the coefficient for coherent interactions in the sample at different potential energies of the source radiation, and the densities of the sample section 30, mold 42, and other intervening structures, a ratio between the intensity of the coherent radiation that would emerge from the sample section 30, mold 42 and other intervening structures present (I(E)), and the intensity of the source radiation received by the detector assembly 22 in the absence of the sample section 30, mold 42, and other intervening structures (IO(E)) can be determined for each potential energy (E) under consideration for the source radiation. In this regard, a model of the transmission of radiation through a material encased in a mold can be represented by the following equation:

$$I(E)=IO(E)\cdot\exp(-\mu wt(E)\cdot\rho w\cdot W1)\cdot NL\cdot(\exp(-\mu st(E)\cdot\rho s\cdot L) -\exp(-\rho s\cdot(\mu st(E)\cdot L+\mu sr(E)\cdot dx)))\cdot\exp(-\mu wt(E)\cdot\rho w\cdot W2);$$

wherein for a given source intensity at the energy E:,

IO(E) is the intensity at the detector of the radiation beam, with no sample or mold present;

I(E) is the intensity of coherent (e.g., Rayleigh) scatter radiation which emerges from the sample section enclosed by mold walls;

$\mu wt(E)$ is the total mass attenuation coefficient in the mold material ($cm^2/g$);

$\rho w$ is the density of the mold material ($g/cm^3$);

W1 is the thickness of the first mold wall 42a (cm);

W2 is the thickness of the second mold wall 42b (cm);

L is the thickness of the sample section 30(cm);

NL is a large integer (e.g., 1000) which partitions the sample length (L) into small segments (dx);

$\mu st(E)$ is the total mass attenuation coefficient in the sample section 30 ($cm^2/g$);

$\rho s$ is the density of the sample section 30 ($g/cm^3$);

$\mu sr(E)$ is the mass attenuation coefficient for coherent (e.g., Rayleigh) radiation scattering in the sample section 30 ($cm^2/g$).

Additional intervening structures, such as a furnace wall, can be accounted for in the equation by adding exponential functions based on the total mass attenuation coefficient of the intervening structure material at energy E, the density of the material, and the thickness of the material. A more complex model could further include the spatial redistribution of radiation during diffraction.

Figure 3:
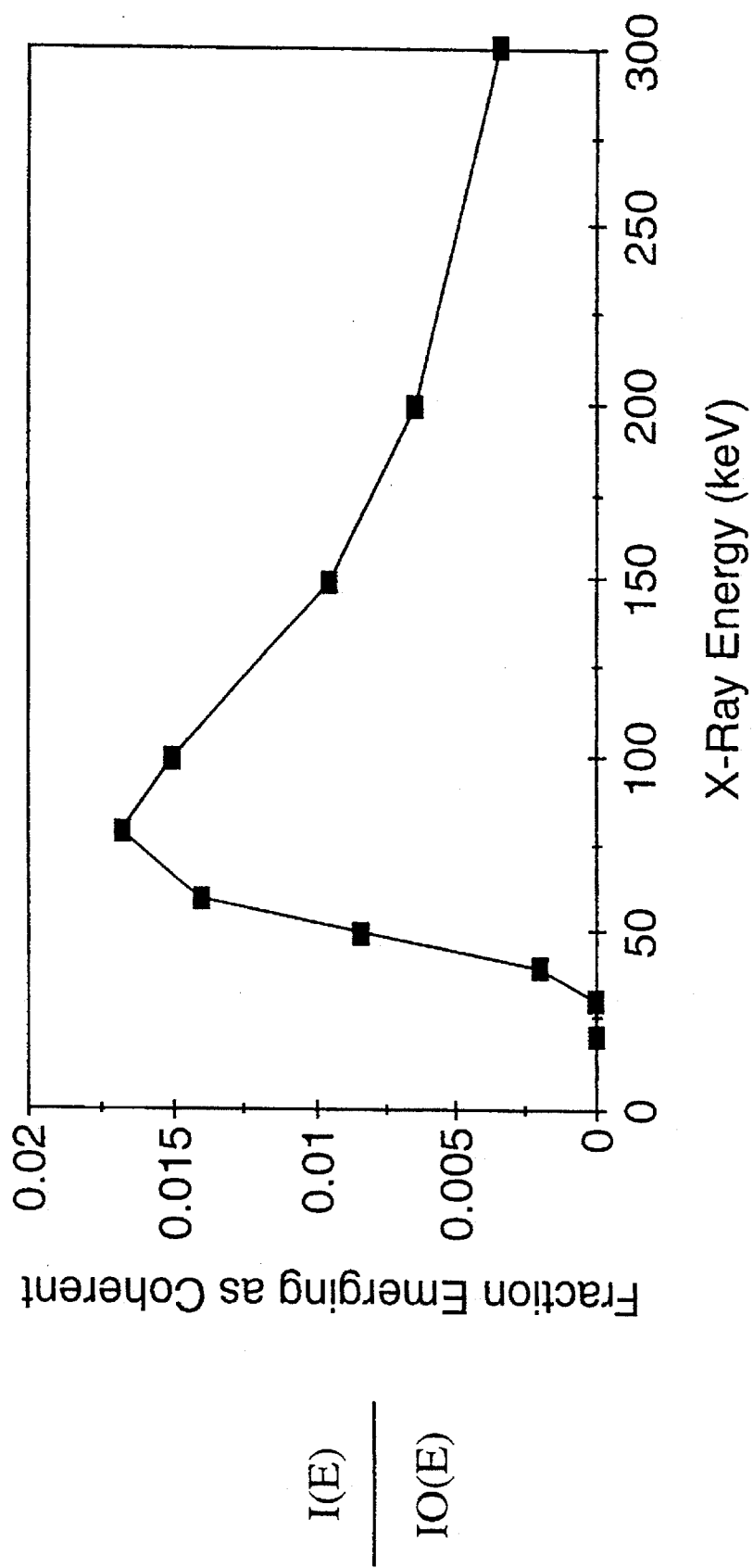
FIG. 3 is a plot of the fraction of diffracted radiation emerging from a mold as coherent radiation as a function of the energy of source radiation.

The various ratios of I(E) to IO(E) can then be plotted as a function of the corresponding potential energies of the source radiation to identify the preferred mean energy of the source radiation. By way of example, FIG. 3 provides such a plot based on an aluminum sample (25 mm thick) encased in an aluminum oxide mold (with 6 mm thick walls). The peak in the plotted curve shows that there is an optimal range of source radiation energies. The optimum energy yields the highest production of diffracted radiation which is able to penetrate through the mold walls 42a,b and sample section 30. Because the mean energy of an x-ray source is generally one-half to one-third of the rated x-ray tube voltage the source preferably uses a tube voltage that is about two to three times the preferred energy peak.

The preferred intensity of the source radiation received by the detector assembly 22 is based on a predetermined minimum detectable radiation level for the particular detector assembly 22 used, the dynamic range of the detector assembly 22, and the ambient noise radiation levels at the detector assembly 22 during operation. As noted above, the intensity of the diffracted radiation received by the detector assembly 22 must be sufficient to permit the diffracted radiation to be distinguished from the noise. As will be appreciated then, the tube current in the radiation source 10 should be selected to achieve the desired intensity at detector assembly 22.

In this regard, the radiation source for diffraction spot imaging preferably is not a microfocus radiation source. In other words, the radiation source preferably has focal spot dimensions larger than about 0.1 mm. Microfocus radiation sources, though useful for thin samples and thin mold walls, have insufficient intensity to provide a detectable transmission diffraction pattern image for the thicknesses of the samples and mold walls normally encountered in casting processes. Microfocus radiation sources typically handle only small electrical currents (e.g., less than about 1 mA) which are often too low to produce the desired intensity of the source radiation for rapid inspection.

As noted, the collimator 14 collimates the divergent source radiation 26 to a small spatial size. Collimators for radiation sources generally are designed using several apertures (in radiation-attenuating material) placed along the source radiation beam path. The aperture dimensions of the collimator are a tradeoff between maximizing the intensity of the radiation beam transmitted (larger aperture size) and minimizing the size of the spatial resolution cell. For example, a radiation beam diameter of 1 mm has been found suitable for a radiation source-to-sample distance of 200 mm (e.g., 0.29 degrees angular aperture). Instead of collimating apertures, the collimator could be comprised of x-ray optic devices which restrict the radiation beam to the desired dimensions. The collimated radiation 46 contains a plurality of substantially parallel rays.

The beam stop 18 is an object composed of a material capable of absorbing a substantial portion of the transmitted (undiffracted) source radiation. A common type of beam stop 18 is composed of tungsten or lead.

The detector assembly 22 may comprise an x-ray imager or merely an energy-sensor, or a combination thereof. An x-ray imager allows for recording/processing of the spatial location of diffracted radiation by measuring the intensity of radiation over a two-dimensional area. An energy-sensitive detector allows for the recording/processing of the diffracted radiation received across the source energy spectrum.

Figure 4:
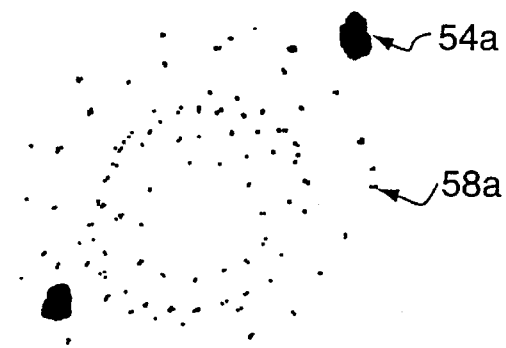
FIGS. 4 and 5 depict diffraction patterns incident upon an x-ray imager for a sample containing crystalline and amorphous phases.
Figure 5:
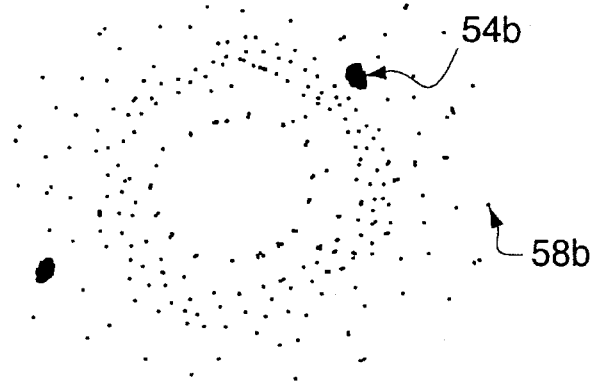

FIGS. 4–5 illustrate the different diffraction patterns received at an x-ray imager for crystalline and amorphous material phases. The x-ray imager shows diffracted radiation from a crystalline phase (e.g., the first diffraction component) as a few spots, and from an amorphous phase (e.g., the second component) as a diffuse ring pattern. Specifically, FIG. 4 has spots 54a representing the first component and a diffuse ring pattern 58a representing the second component. FIG. 5 has less intense spots 54b from the first component and a more intense diffuse ring pattern 58b from the second component, indicating that the sample section examined in FIG. 4 has a greater volume of crystalline phase and a smaller volume of amorphous phase than the sample section examined in FIG. 5. The x and y axes of FIGS. 4 and 5 reflect spatial coordinates of the diffracted radiation received by the imager.

Figure 6:
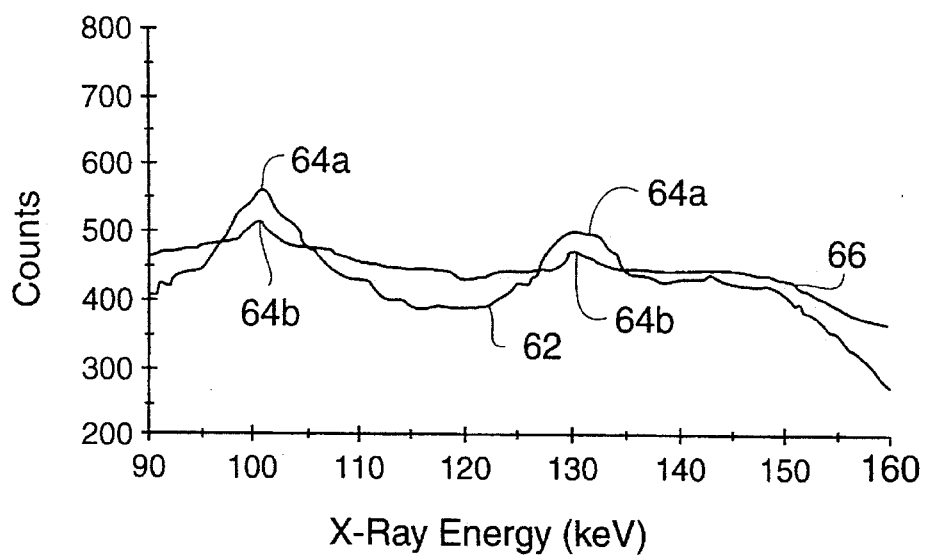
FIG. 6 is a plot of the intensity detected by an energy detector versus the energy of the source radiation at two time intervals for a sample containing crystalline and amorphous phases.

Referring to FIG. 6, the output of an energy sensitive detector is depicted versus the energy of the source radiation at two time intervals. More particularly, FIG. 6 plots the quantity of photons (or counts) interacting with the energy detector during a given time period versus the energy of the photons (i.e., corresponding with the radiation source energy spectrum). Peaks 64a,b correspond to the spots 54a,b, respectively, of FIGS. 4–5. The height of the peaks corresponds to the first component and thus to the amount of crystalline phase in the sample. Accordingly, curve 62 corresponds to a greater amount of crystalline phase in the sample than curve 66.

The unique Laue diffraction pattern of crystalline phases relative to amorphous phases is explained by the Bragg equation. The spots represent diffracted radiation that is a solution to the Bragg equation:

$$\frac{1.24n}{E} = n\lambda = 2d\sin\theta$$

where, n is an integer;

E is the energy (keV) of the source radiation which is diffracted;

$\lambda$ is the wavelength (nm) of the incident source radiation which is diffracted;

d is the lattice spacing (nm) in the crystal structure of the crystalline phase.

$\theta$ is the angle between the lattice plane and the incident radiation.

For a given orientation of the crystalline phase, diffracted radiation that is a solution to the Bragg equation forms spots 54a,b on the diffraction pattern. In contrast, the disordering of the amorphous phase produces the diffuse ring pattern 58a,b.

A detector assembly 22 utilizing the x-ray imager has different components from a detector assembly utilizing an energy-sensitive detector. A detector assembly 22 utilizing an x-ray imager generally includes a scintillator, an image intensifier, and a charge coupled device video imager. A detector assembly 22 utilizing an energy-sensitive detector includes the detector (which is preferably a cooled, intrinsic germanium detector with an integral FET preamplifier), a high voltage detector bias supply, a linear spectroscopy amplifier, and a multichannel analyzer. The components of the detector assembly preferably are optimized for high sensitivity in the 40 to about 500 keV range with a high count rate (e.g., greater than about 100,000 counts/sec) capability. Energy-sensitive detectors generally provide a higher sensitivity than the x-ray imager and thus require a lower intensity x-ray source.

The monitoring system in FIG. 1 is set to accommodate a transmission-type diffraction pattern. As will be appreciated, the system could also be arranged to accommodate a back reflection-type diffraction pattern in which the diffraction pattern is received by a detector assembly located on the radiation source side of the sample, or to accommodate a glancing incidence-type diffraction pattern in which the diffraction pattern is received by the detector assembly located at the side of the sample. The transmission-type Laue diffraction pattern is preferred as the diffraction patterns produced by the other two configurations are produced by diffracted radiation that may not have passed completely through the sample. It is important for the pattern to be produced by radiation passing completely through the sample to accurately locate the interface between the crystalline and amorphous phases at all locations within the casting cross-section. Additionally, the transmission mode is necessary to assess the relative crystalline/amorphous phase fractions along the radiation beam path.

Referring again to FIG. 1, the operation of a casting process using the present invention will now be described. The description will be based upon the use of the invention in the casting of single-crystal or directionally-solidified parts.

The casting process is commenced by placing the molten material into the mold 42 which rests on a chilled surface (not shown). The mold 42 is contained within an induction or resistance-heated furnace (not shown) and is slowly withdrawn from the furnace as crystallization progresses upwards from the chilled surface.

Source radiation 26 is generated by the radiation source 10, restricted spatially by the collimator 14 and directed through the following: the mold wall 42a, a portion of the amorphous phase 38, the interface between the amorphous and crystalline phases, and a portion of the crystalline phase 34. The source radiation interacts with the crystalline and amorphous phases in the sample section to produce diffracted radiation having the first component 50 associated with the crystalline phase and the second component 52 associated with the amorphous phase.

At least a portion of the first and second components are received by the detector assembly 22 which provides an output signal related to the received portion of one and preferably each of the first and second components. The output signal is used to monitor the interface between the crystalline and amorphous phases.

The output signal can be used to estimate the position of the interface in the mold and/or the degree of crystallization of the crystalline phase. To do this, the first component may be compared to the second component at selected time intervals. For example, at a first time interval the source radiation may be scanned vertically up and down the mold to locate either (i) the interface between the portion of the sample that is entirely an amorphous phase and that which has both amorphous and crystalline phases (e.g., the top of the dendrites 36) and/or (ii) the interface between the portion of the sample that is entirely a crystalline phase and that which has both amorphous and crystalline phases (e.g., the base of the dendrites 36). At a second time interval, the above-noted interfaces are again located. The distance between the interface at the first time interval and the interface at the second time interval divided by the period between the first and second time intervals provides the rate of crystallization.

The first and second components can also be measured for a defined area of the sample during different time intervals to estimate the rate of crystallization. For example, the first and second components are compared with one another during a first time interval to determine a first degree of crystallization of the crystalline phase and during a second time interval to determine a second degree of crystallization of the crystalline phase. The comparison can be based on the relative intensities or magnitudes of the first and second components. The crystallization rate can be determined based on the first and second degrees of crystallization and the period between the time intervals.

As will be appreciated, computed tomography can be applied to data regarding the position and/or crystallization rate to generate a two- or three-dimensional representation of the interface between the amorphous and crystalline phases. Computed tomography using the first and second components of diffraction will yield tomography images with higher contrast between crystalline and amorphous phases than computed tomographic images based on exploiting the small density differences between the crystalline and amorphous phases. Such an image could be generated during discrete time intervals to more precisely control the casting process or to verify casting-process models.

Based on the position and/or crystallization rate, a monitor signal can be provided to control the casting process. The monitor signal can be used to control selected parameters in the casting process, such as the temperature of the furnace and/or the rate of withdrawal of the mold from the furnace (e.g., the duration of the casting), and the like. The monitor signal can be manually or automatically generated. To automatically generate the monitor signal, the first and second components or the interface position or crystallization rate can be compared against predetermined values corresponding to each time interval during which the measurements are taken. If the measurement exceeds a maximum predetermined value (e.g., the rate of crystallization is too fast) or is less than a minimum predetermined value (e.g., the rate of crystallization is too slow), an appropriate monitor signal is generated to adjust the casting process.

To form the desired diffraction patterns, the source radiation should be collimated. Preferably, the intensity of the portion of the first component received by the detector assembly and the portion of the second component received by the detector assembly together is at least about 0.1% of the intensity of the source radiation.

The monitor signal can be used to cause a portion of the mold to be heated to a second temperature greater than a first temperature of the mold to remelt a portion of the crystalline phase. After the portion of the crystalline phase is remelted, the portion of the mold can be cooled to a third temperature less than the second temperature to recrystallize the remelted portion of the crystalline phase. It is believed that the remelting and recrystallization of the defective portions of the crystalline phase is an effective solution to decrease the number of castings which must be discarded for crystalline defects.

As will be appreciated, the present invention is not necessarily limited to casting processes but can be used in any process to monitor the position of the interface between a crystalline phase and an amorphous phase, such as a liquid, or any other process involving an interface between a crystalline and another crystalline or an amorphous phase. The present invention can thus be used to monitor solidification processes, such as the casting of metals and alloys, growth of semiconductor boules, chemical precipitation processes, such as those in which crystalline precipitates are formed at high temperatures in an amorphous phase.

By way of example, the present invention can detect the formation of a second crystalline phase in a crystalline structure. The second crystalline phase has a different crystal structure than the surrounding crystal. The formation of a second crystalline phase in a surrounding crystalline phase is employed in the alloying of metals. The formation of the second crystalline phase would produce diffracted radiation different from the diffracted radiation produced by the surrounding crystalline phase in the absence of the second crystalline phase. The diffraction pattern of the second crystalline phase can be isolated by taking into account the diffraction pattern produced by the surrounding crystalline phase in the absence of the second crystalline phase.

Additionally, the present invention can be used to detect defects in the crystal structure of the crystalline phase during casting. A material having multiple crystals will produce a diffraction pattern distinct from a crystalline phase having only one crystal. For example, a crystalline having multiple crystals will produce more spots than a crystalline phase having only one crystal. In the event that more than one crystal is detected in a monocrystalline phase would enable the casting process to be altered to remelt the portion of the material having more than one crystalline structure followed by resolidification of the crystalline phase. In this matter, the portion of the castings discarded for crystalline defects can be significantly reduced.

EXPERIMENT 1

A small piece of directionally-solidified turbine blade alloy was polished to make the directional nature of the microstructure observable. Incident x-ray beam and film plane angles were adjusted to 45° to give an angle of 90° between the x-ray beam and imager. A definite x-ray diffraction pattern was obtained using a 50 kVp x-ray tube voltage. The x-ray tube voltage was increased to 75 kVp, then to 100 kVp and finally to 150 kVp. The diffraction pattern persisted, with a very noticeable increase in intensity. The Compton scattering background increased somewhat with tube voltage increases. This experiment verifies that x-ray diffraction can be obtained with x-ray tube voltages (100 kVp and 150 kVp) which are substantially higher than that used in conventional (40 kVp) Laue measurements.

EXPERIMENT 2

Experiment 1 was repeated with a 6 mm-thick piece of mold material typically used for single-crystal turbine blade castings (a mixture of aluminum oxide, silicon oxide, and zirconium oxide) in a position between the source radiation and the turbine-blade alloy specimen. At an x-ray tube voltage of 150 kVp, many of the diffraction spots near the beam stop (small-angle diffraction) remained. The experiment confirms the ability to perform transmission diffraction even through typical casting mold material.

EXPERIMENT 3

A series of heating, melting, and recrystallization experiments were conducted using x-rays to locate the advancing and receding interface between the solidified metal and molten metal. A 22-millimeter-diameter polycrystalline 99.999% aluminum rod was placed in a quartz tube in a furnace. The rod was heated to (652° C.) (near the melting point) and the changing transmission Laue diffraction pattern was observed. The specimen was then cooled and sectioned for analysis.

Another experiment was conducted in which the aluminum rod was melted and resolidified. Real-time x-ray diffraction was employed to follow the progression of the interface between the solidified aluminum and the molten aluminum. The difference between the pattern generated by the high-temperature solid aluminum and the pattern generated by the liquid aluminum was dramatic and unmistakable. The diffraction spots from the solid disappeared as a diffuse ring formed when the aluminum was fully melted.

EXPERIMENT 4

A copper rod was placed in a quartz tube, with a triangular cross-section. The tube was then inserted into a gradient furnace. A 1 millimeter diameter, collimated x-ray beam was directed into the furnace, and a real-time x-ray imager was placed on the opposite side of the furnace. A 6 millimeter thick, 3 millimeter diameter tungsten disk was positioned in the center of the primary x-ray beam emerging from the furnace to act as a beam stop. X-rays diffracted from the copper sample in the furnace passed to the sides of the beam stop and were imaged.

The furnace was manipulated remotely to move it vertically and horizontally. The vertical movement was used to scan the x-ray beam and imager with respect to the liquid/solid copper boundary that was established in the gradient furnace. Horizontal movement across the wedge-shaped copper specimen permitted interrogating different thicknesses.

The temperature of the furnace was raised to melt the copper and then lowered to solidify it. The warming and cooling sequence was repeated several times. As in the aluminum melting experiments, the solid copper produced a diffraction image with bright diffraction spots. When the melting temperature of copper was exceeded, the ordered diffraction pattern disappeared and was replaced by a diffuse ring of x-ray scattering from the molten copper. This experiment validated the sensing method for locating a liquid/solid boundary in a metal sample with physical characteristics (atomic number and density) similar to that of nickel-based alloys.

EXPERIMENT 5

A gallium sample was placed in a container capable of producing a temperature gradient. A temperature controller was connected to the heater to produce a steady-state boundary between the solid gallium (at the top because its density is less than the liquid gallium) and the liquid gallium. The position of the probing x-ray beam was moved into the solid or liquid by a remote positioning fixture. X-ray diffraction images and radiographic images (by removing the collimating apertures in the x-ray beam) were alternatively taken. The density variation between the solid and liquid gallium is great enough to produce a discernable difference in brightness in a radiographic image. The ability to independently determine by radiographic image the position of the liquid/solid boundary (brighter versus darker regions of the radiograph) provided a means for validating the spatial performance of the x-ray imager.

When the x-ray imager sensor was positioned to probe only the solid gallium, bright diffraction spots were observed. In the liquid, the diffuse scattering ring was observed. At intermediate locations between liquid and solid, the diffuse ring and diffraction spots were present, but both with decreased intensity in rough ratio to their relative amounts. The radiographic images produced with the x-ray images validated that the x-ray imager could accurately locate the position of the liquid/solid interface, and verified that the spatial resolution of the diffraction sensor is approximately the size of the source radiation beam at the sample.

EXPERIMENT 6

The x-ray imager was replaced by an energy-sensitive detector (intrinsic germanium). The much higher efficiency of the detector, compared to the imager, required the replacement of the collimating apertures. The 1-millimeter diameter aperture, used in experiments with the x-ray imager, produced too intense a diffracted beam for the germanium detector. A 0.2 millimeter diameter aperture was used. A source-sample distance of 250 millimeters and a sample-detector spacing of 180 millimeters was used for the experiments. The spectra were obtained with an x-ray tube potential of 160 kV and a tube current of 1 mA.

Spectral peaks at approximately 100 keV and 130 keV were produced by x-ray diffraction spots in a solid gallium sample. There were no discernable peaks in the 100–130 keV spectrum recorded when the x-ray diffraction pattern in a liquid gallium specimen was examined. Although the intensity (x-rays per unit area per second) was higher for the diffraction spots, the spots were highly localized. The spectrum for the liquid specimen, in contrast, recorded more counts overall in each energy interval although the peak intensity was lower.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A method for monitoring an interface between a crystalline phase and an amorphous phase of a material within a container, comprising the steps of:

directing source radiation through at least one wall of a container and into an interface between a portion of a crystalline phase of a material and a portion of an amorphous phase of said material contained in said container to provide diffracted radiation having a first diffraction component with a first spatial radiation distribution associated with said crystalline phase and a second diffraction component with a second spatial radiation distribution associated with said amorphous phase, said first and second spatial radiation distributions being spatially distinct;

receiving at least a portion of at least one of said first diffraction component and said second diffraction component of said diffracted radiation on a radiation sensitive detector means located outside of said container to provide an output signal, said output signal including information corresponding to said spatial radiation distribution of the received portion; and using said output signal to monitor said interface between said crystalline phase and said amorphous phase.

2. The method as, claimed in claim 1, wherein:

said amorphous phase is a liquid phase of said material.

3. The method as claimed in claim 2, wherein said material has a variable rate of crystallization, and said using step comprises:

comparing during a first time interval a first output signal component corresponding with said first diffraction component with a second output signal component corresponding with said second diffraction component to provide a first compared value;

comparing during a second time interval said first output signal component with said second output signal component to provide a second compared value; and employing said first and second compared values to determine said rate of crystallization between said first and second time intervals.

4. The method as claimed in claim 1, wherein said receiving step comprises:

receiving both said first diffraction component and said second diffraction component on said radiation sensitive detector means.

5. The method as claimed in claim 4, wherein said container is a casting mold.

6. The method as claimed in claim 1, wherein said directing step comprises:

varying the intensities of said first and second diffraction components over time by changing the spatial location of said source radiation in a defined volume of said material.

7. The method as claimed in claim 1, wherein said receiving step comprises:

generating for successive time intervals corresponding successive values relating to at least one of a first output signal component corresponding with said first diffraction component and a second output signal component corresponding with said second diffraction component.

8. The method as claimed in claim 7, wherein said using step comprises:

comparing said successive values with a predetermined completion value that corresponds with a degree of crystallization completion.

9. The method as claimed in claim 7, wherein said using step comprises:

employing said successive values to determine a rate of crystallization.

10. The method as claimed in claim 9, wherein said using step comprises:

comparing said rate of crystallization to a predetermined value.

11. The method as claimed in claim 7, wherein said successive values corresponding to said first output signal component and said successive values increase in magnitude over said successive time intervals.

12. The method as claimed in claim 7, wherein said successive values corresponding to said second output signal component and said successive values decrease in magnitude over said successive time intervals.

13. The method as claimed in claim 7, wherein:

said first and second output signal components correspond to the intensity of said first and second diffraction components, respectively.

14. The method as claimed in claim 1, wherein said source radiation is passed through a defined region of said container and said using step comprises:

comparing a first output signal component corresponding with said first diffraction component with a second output signal component corresponding with said second diffraction component to determine the portion of said defined region occupied by at least one of said crystalline phase and said amorphous phase.

15. The method as claimed in claim 1, wherein said using step comprises:

comparing during a first time interval a first output signal component corresponding with said first diffraction component and a second output signal component corresponding with said second diffraction component to locate said interface at a first position;

comparing during a second time interval said first and second output signal components to locate said interface at a second position; and employing said first and second positions to determine a monitor signal.

16. The method as claimed in claim 15, wherein said first and second output signal components correspond to a time interval and said using step comprises:

comparing said output signal to a predetermined completion value.

17. The method as claimed in claim 1, wherein said receiving step comprises:

comparing said first and second spatial radiation distributions to provide said output signal.

18. The method as claimed in claim 17, wherein said using step comprises:

using said monitor signal to establish at least one casting process control parameter.

19. The method as claimed in claim 17, wherein said using step comprises:

using said monitor signal to control in real time at least one casting process control parameter.

20. The method as claimed in claim 17, further comprising:

using said monitor signal to control at least one of the following parameters: the temperature of a furnace containing said crystalline and amorphous phases and the rate of withdrawal of said crystalline phase from said furnace.

21. The method as claimed in claim 1, wherein a portion of said container is at a first temperature and further comprising:

heating in response to said output signal said portion of said container to a second temperature greater than said first temperature to remelt a portion of said crystalline phase.

22. The method as claimed in claim 21, further comprising:

cooling in response to said output signal said portion of said container to a third temperature less than said second temperature to recrystallize said remelted portion of said crystalline phase.

23. The method as claimed in claim 1, wherein:

said source radiation and the radiation sensitive detector means are positioned on opposing sides of said material to produce transmission-type diffraction in said first and second diffraction components.

24. The method as claimed in claim 1, wherein said material crystallizes in a substantially vertical direction and wherein:

said directing step comprises:

moving the source radiation relative to the container in a substantially vertical direction to monitor the progression of the interface over time.

25. The method as claimed in claim 1, further comprising:

using at least one of a first output signal component corresponding with said first diffraction component and a second output signal component corresponding with said second diffraction component to perform computed tomography and generate a two- or three- dimensional representation of the interface between the crystalline and amorphous phases.

* * * * *